US00PP31783P2

(12) United States Plant Patent
Shafer

(10) Patent No.: US PP31,783 P2
(45) Date of Patent: May 19, 2020

(54) ***PETUNIA* PLANT NAMED 'BALCUSHWARE'**

(50) Latin Name: ***Petunia* x *hybrida***
Varietal Denomination: Balcushware

(71) Applicant: Ball Horticultural Company, West Chicago, IL (US)

(72) Inventor: Gail Shafer, Santa Maria, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/501,919

(22) Filed: Jul. 3, 2019

(51) Int. Cl.
*A01H 5/02* (2018.01)
*A01H 6/82* (2018.01)

(52) U.S. Cl.
USPC ..... Plt./356.1
CPC ..... *A01H 6/82* (2018.05)

(58) Field of Classification Search
USPC ..... Plt./356.1, 356.23
CPC ..... A01H 5/02
See application file for complete search history.

(56) References Cited

PUBLICATIONS http://taes.utk.edu/upload/WTREC/2019SpringSalePlantList.pdf; May 4, 2019; 2 pages.*
https://garden.org/plants/view/783454/Petunia-ColorRush-Watermelon-Red/; Jan. 14, 2020; 4 pages.*

* cited by examiner

*Primary Examiner* — Kent L Bell
(74) *Attorney, Agent, or Firm* — Audrey Charles

(57) ABSTRACT

A new and distinct cultivar of *Petunia* plant named 'Balcushware', characterized by its medium pinkish-red colored flowers, dark green-colored foliage, and vigorous, mounded-spreading growth habit, is disclosed.

1 Drawing Sheet

Latin name of genus and species of plant claimed: *Petunia* x *hybrida*.

Variety denomination: 'Balcushware'.

BACKGROUND OF THE INVENTION

The present invention relates to a new and distinct cultivar of *Petunia* plant botanically known as *Petunia* x *hybrida* and hereinafter referred to by the cultivar name 'Balcushware'.

The new cultivar originated in a controlled breeding program in Arroyo Grande, Calif. during July 2013. The objective of the breeding program was the development of *Petunia* cultivars with single-type flowers, unique flower coloration and patterns, and vigorous, mounded-spreading growth habit.

The new *Petunia* cultivar is the result of cross-pollination. The female (seed) parent of the new cultivar is the proprietary *Petunia* x hybrid breeding selection coded GS-9615-3, not patented, characterized by its medium red-colored flowers, medium green-colored foliage, and vigorous, mounded-spreading growth habit. The male (pollen) parent of the new cultivar is the proprietary *Petunia* x hybrid breeding selection coded GS-9403-8, not patented, characterized by its dark pink-colored flowers, medium green-colored foliage, and vigorous, mounded-spreading growth habit. The new cultivar was discovered and selected as a single flowering plant within the progeny of the above stated cross-pollination during May 2014 in a controlled environment in Arroyo Grande, Calif.

Asexual reproduction of the new cultivar by terminal stem cuttings since May 2014 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcushware' as a new and distinct cultivar of *Petunia* plant:

1. Medium pinkish-red colored flowers;
2. Dark green-colored foliage; and
3. Vigorous, mounded-spreading growth habit.

Plants of the new cultivar differ from plants of the female parent primarily in having more pink in the flower color and darker green-colored leaves. Plants of the new cultivar differ from plants of the male parent primarily in having more red in the flower color and darker green-colored leaves.

Of the many commercially available *Petunia* cultivars, the most similar in comparison to the new cultivar is SUPERTUNIA VISTA Fuchsia 'BHTUN65301', U.S. Plant Pat. No. 28,457. However, in side-by-side comparisons, plants of the new cultivar differ from plants of 'BHTUN65301' in at least the following characteristics:

1. Plants of the new cultivar have a flower color that is less purple-colored than plants of 'BHTUN65301'; and
2. Plants of the new cultivar have flowers with larger diameter corollas than plants of 'BHTUN65301'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balcushware'. The plants were approximately 4 months old and grown in 6-inch pots for approximately 12 weeks in a greenhouse in West Chicago, Ill. Plants were given one pinch at transplant.

DETAILED BOTANICAL DESCRIPTION

Figure 1:
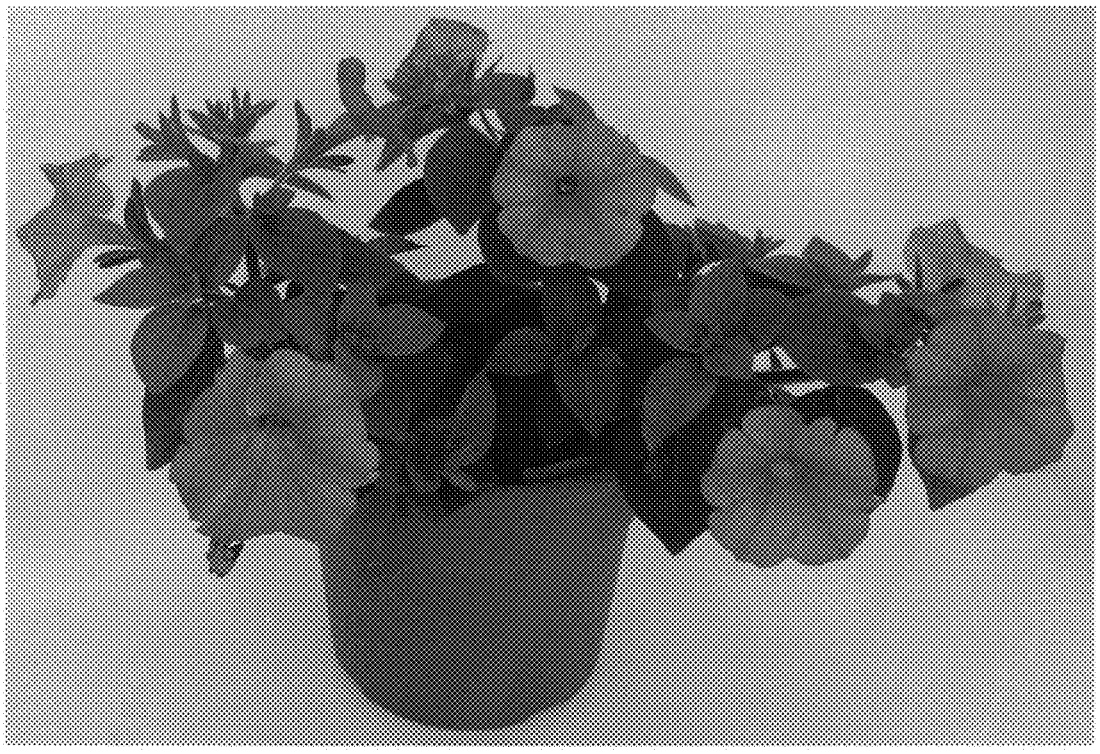
FIG. 1 illustrates a side view of the overall growth and flowering habit of 'Balcushware'.
Figure 2:
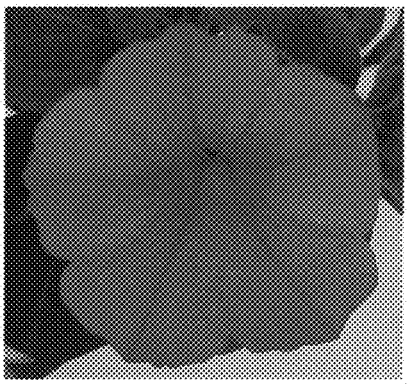
FIG. 2 illustrates a close-up view of an individual flower of 'Balcushware'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2019 under natural light conditions in West Chicago, Ill.

The following descriptions and measurements describe approximately 4-month old plants produced from cuttings from stock plants and grown in a glass-covered greenhouse under conditions comparable to those used in commercial practice. The plants were grown in West Chicago, Ill. in 6-inch pots for approximately 12 weeks utilizing a soilless growth medium. Plants were given one pinch at transplant. Greenhouse temperatures were maintained at approximately 67° F. to 72° F. (19° C. to 22° C.) during the day and approximately 65° F. to 68° F. (18° C. to 20° C.) during the night. Supplemental lighting was used. Measurements and numerical values represent averages of typical plants.

Botanical classification: *Petunia* x *hybrida* 'Balcushware'.

Parentage:

*Female parent*.—Proprietary *Petunia* x hybrid breeding selection coded GS-9615-3, not patented.

*Male parent*.—Proprietary *Petunia* x hybrid breeding selection coded GS-9403-8, not patented Propagation:

*Type cutting*.—Terminal stem.

*Time to initiate roots*.—Approximately 6 to 9 days.

*Time to produce a rooted cutting*.—Approximately 21 to 28 days.

*Root description*.—Fibrous.

*Rooting habit*.—Freely branching.

Plant description:

*Commercial crop time*.—Approximately 6 to 8 weeks from a rooted cutting to finish in an 11 cm pot.

*Growth habit and general appearance*.—Vigorous, mounded-spreading.

*Size*.—Height from soil level to top of plant plane: Approximately 18.0 cm. Width: Approximately 62.0 cm.

*Branching habit*.—Freely branching, pinching improves basal branching. Quantity of main branches per plant: Approximately 3.

*Branch*.—Strength: Moderate. Length: Approximately 30.0 cm. Diameter: Approximately 6.0 mm. Length of central internode: Approximately 1.8 cm. Texture: Densely glandular pubescent with a mixture of long and short hairs. Gland color: Colorless. Color of young and mature stems: 144A.

Foliage description:

*General description*.—Quantity of leaves per main branch: Approximately 20. Fragrance: Slight. Form: Simple. Arrangement on flowering stem: Opposite.

*Leaves*.—Aspect: Acute angle to stem. Shape: Ovate. Margin: Entire. Apex: Acute. Base: Rounded. Venation pattern: Pinnate. Length of mature leaf: Approximately 5.5 cm. Width of mature leaf: Approximately 4.5 cm. Texture of upper and lower surfaces: Densely glandular pubescent. Gland color: Colorless. Color of upper surface of young and mature foliage: 137A with venation of 147C to indistinguishable. Color of lower surface of young and mature foliage: Closest to 138A with venation of 147C to indistinguishable.

*Petiole*.—Length: Approximately 0.3 mm. Width: Approximately 3.0 mm. Texture: Densely glandular pubescent with a mixture of long and short hairs. Gland color: Colorless. Color: 147C.

Flowering description:

*Flowering habit*.—'Balcushware' is freely flowering under outdoor growing conditions with substantially continuous blooming from spring through autumn and year-round in greenhouse environment.

*Lastingness of individual flower on the plant*.—Approximately 10 to 12 days.

Flower description:

*General description*.—Type: Simple, salverform. Quantity per plant: Approximately 23. Fragrance: Slight.

*Bud*.—Rate of opening: Generally takes 2 to 3 days for bud to progress from first color to fully open flower. Quantity per plant: Approximately 12.

*Bud just before opening*.—Shape: Oblong. Length: Approximately 3.8 cm. Diameter at apex: Approximately 8.0 mm. Diameter at base: Approximately 2.0 mm. Texture: Densely glandular pubescent. Gland color: Colorless. Color of petal portion: N77B with venation of 146C. Color of tube: Closest to 182C with venation of 146C.

*Corolla*.—Diameter: Approximately 6.0 cm.

*Petals*.—Quantity: 5, fused to form a tube. Shape: Obovate. Appearance: Dull. Margin: Entire, moderately wavy. Apex: Broadly cuspidate, occasionally with three tips. Length from tube: Approximately 2.7 cm. Length of free portion: Approximately 1.1 cm. Width: Approximately 3.0 cm. Texture of upper surface: Glabrous. Texture of lower surface: Sparsely glandular pubescent. Gland color: Colorless. Color of upper surface when first open: 52A to 52B with midveins of 53A. Color of lower surface when first and fully open: Closest to 186D with venation of 146C. Color of upper surface when fully open: 50A with 54B to 54C, midveins of N186C.

*Corolla tube*.—Length: Approximately 3.0 cm. Diameter at distal end: Approximately 1.0 cm. Diameter at proximal end: Approximately 2.0 mm. Texture of inner surface: Glabrous. Texture of outer surface: Densely glandular pubescent. Gland color: Colorless. Color of inner surface: 186C with venation of N186C. Color of outer surface: Closest to 182D with venation of 146D.

*Sepals*.—Quantity per flower: 5, fused at base. Shape: Linear. Margin: Entire. Apex: Acute. Length: Approximately 2.5 cm. Width: Approximately 5.0 mm. Texture of upper and lower surfaces: Densely glandular pubescent. Gland color: Colorless. Color of upper surface: 137A. Color of lower surface: 138A with 144A at base.

*Peduncle*.—Strength: Strong, flexible. Aspect: Acute angle to stem. Length: Approximately 2.8 cm. Diameter: Approximately 2.0 mm. Texture: Densely glandular pubescent with a mixture of long and short hairs. Gland color: Colorless. Color: 144A.

*Reproductive organs*.—Androecium: Stamen quantity: 5, basifixed. Stamen length: Approximately 2.0 cm. Filament length of fixed portion: Approximately 1.2 cm. Filament color: NN155D with a heavy overlay of 146D at the center and a very faint tint of 86A at anther attachment. Anther shape: Bilobed. Anther length: Approximately 1.0 mm. Anther color: NN155C. Pollen amount: Abundant. Pollen color: NN155B. Gynoecium: Pistil quantity: 1 per flower. Pistil length: Approximately 2.2 cm. Stigma shape: Funnel. Stigma length: Approximately 1.0 mm. Stigma color: 146A. Style length: Approximately 1.8 cm. Style color: 145C. Ovary length: Approximately 3.0 mm. Ovary color: 144A.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balcushware', substantially as herein illustrated and described.

* * * * *